United States Patent

Schaus et al.

[11] Patent Number: 6,069,152
[45] Date of Patent: May 30, 2000

[54] 5-HT₄ AGONISTS AND ANTAGONISTS

[75] Inventors: John M. Schaus, Zionsville; Marlene L. Cohen, Carmel; Dennis C. Thompson, Indianapolis, all of Ind.

[73] Assignee: Eli Lilly and Company, Indianapolis, Ind.

[21] Appl. No.: 08/946,495

[22] Filed: Oct. 7, 1997

[51] Int. Cl.⁷ .............. A61K 31/445; A61K 31/495; C07D 231/56; C07D 401/12
[52] U.S. Cl. ........................................... 514/322; 546/199
[58] Field of Search ............................... 546/199; 514/322

[56] References Cited

U.S. PATENT DOCUMENTS

| | | | |
|---|---|---|---|
| 3,145,215 | 8/1964 | Kirchner | 546/199 |
| 5,552,398 | 9/1996 | King et al. | 514/214 |

FOREIGN PATENT DOCUMENTS

| | | |
|---|---|---|
| 230718 | 8/1987 | European Pat. Off. |
| 0347749 | 12/1989 | European Pat. Off. |
| 0358903 | 3/1990 | European Pat. Off. |
| 0410509 | 1/1991 | European Pat. Off. |
| 0491664 | 6/1992 | European Pat. Off. |
| 0623621 | 11/1994 | European Pat. Off. |
| 93/03725 | 3/1993 | WIPO . |
| 93/24117 | 12/1993 | WIPO . |
| 94/00113 | 1/1994 | WIPO . |
| 94/07859 | 4/1994 | WIPO . |
| 94/27987 | 12/1994 | WIPO . |
| 96/38420 | 5/1996 | WIPO . |

OTHER PUBLICATIONS

Robert W. Hamilton, *J. Heterocyclic Chem.*, 13, 545–553 (1976).
Kaumann, et al., *Bio. Med. Chem. Let.*, 2, 419–420 (1992).
Derwent Abstract, Belgium 770068 (1970).
Derwent Abstract, Japanese 8081–858 (1972).

*Primary Examiner*—Ceila Chang
*Attorney, Agent, or Firm*—Gilbert T. Voy

[57] ABSTRACT

Compounds of formula I:

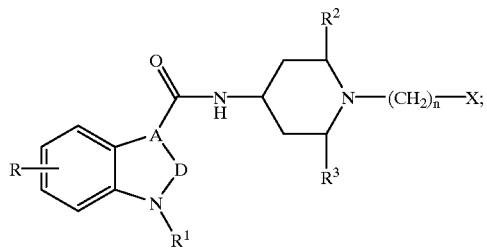

are used as antagonists and partial agonists for the serotonin receptor 5-HT₄ and provide therapeutic methods for treatment of disorders caused by or affected by dysfunction of the 5-HT₄ receptor.

12 Claims, No Drawings

5-HT$_4$ AGONISTS AND ANTAGONISTS

FIELD OF THE INVENTION

The present invention belongs to the fields of pharmacology and medicinal chemistry, and provides a series of indazole- and 2-oxobenzamidazole-3-carboxamides which are antagonists of the serotonin 5-HT$_4$ receptor.

BACKGROUND OF THE INVENTION

Processes in the brain and other organs involving serotonin as a neurotransmitter have been a major field of pharmacological research for some decades. A large number of processes which depend on serotonin have been identified, and numerous therapeutic compounds which affect such processes are in widespread use. More than a dozen receptors which are acted upon by serotonin have been identified. Some of the receptors' physiological mechanisms have been identified, and others are still the subject of extended and active research.

One of the more recently identified serotonin receptors is known as 5-HT$_4$. Bockaert J., Fozard J., Dumuis A., et al., "The 5-HT$_4$ Receptor: A Place in the Sun", *Trends Pharmacol. Sci.*, 13, 141, 1992. Therapeutic methods making use of the 5-HT$_4$ receptor have been held back by the lack of compounds which affect the 5-HT$_4$ receptor without substantial effect at other receptors. The present invention provides a series of new pharmaceutical agents which have a high affinity at the 5-HT$_4$ receptor.

SUMMARY OF THE INVENTION

The present invention provides compounds of formula I:

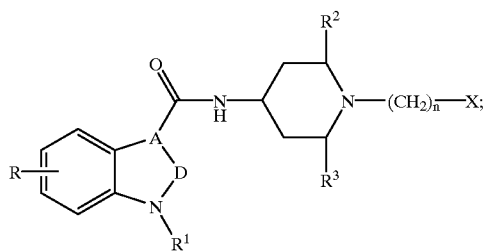

wherein:
A—D is C=N or N—C=O;
n is 1, 2, 3, 4, or 5;
R is hydrogen, halo, C$_1$–C$_4$ alkyl, hydroxy, C$_1$–C$_4$ alkoxy, C$_1$–C$_4$ alkylthio, cyano, trifluoromethyl, carboxamido, mono or di(C$_1$–C$_4$ alkyl)carboxamido;
R$^1$ is hydrogen, C$_1$–C$_6$ alkyl, C$_3$–C$_6$ cycloalkyl, or substituted C$_3$–C$_6$ cycloalkyl;
R$^2$ and R$^3$ are each hydrogen or taken together form a bridge of 1 to 4 methylene units;
X is OR$^4$ or NR$^4$R$^5$;
R$^4$ is hydrogen, C$_1$–C$_6$ alkyl, C$_3$–C$_6$ cycloalkyl, substituted C$_3$–C$_6$ cycloalkyl, phenyl, substituted phenyl, (C$_1$–C$_6$ alkyl)CO, benzoyl, substituted benzoyl, tricyclo[3.3.1.1$^{3,7}$]decan-1-oyl, or S(O)$_2$R$^6$;
R$^5$ is hydrogen or R$^4$ and R$^5$ together with the nitrogen to which they are attached form a 1-pyrrolidinyl, 1-piperazinyl, 1,2,3,4-tetrahydro-2-isoquinolinyl, 2,3-dihydro-1-indolinyl, 4-morpholinyl, 1-piperidinyl, 1-hexamethyleneiminyl, or a phthalimidyl ring;
R$^6$ is C$_1$–C$_6$ alkyl, C$_3$–C$_6$ cycloalkyl, substituted C$_3$–C$_6$ cycloalkyl, phenyl, or substituted phenyl;
or a pharmaceutically acceptable salt thereof.

The invention further provides pharmaceutical formulations comprising the above compounds and a pharmaceutically acceptable carrier, and provides pharmaceutical methods comprising the use of the compounds of formula I.

The pharmaceutical methods of the present invention include a method of affecting the 5-HT$_4$ receptor, and in particular of providing partial agonist and antagonist activity at that receptor. Accordingly, the invention provides methods for the treatment or prophylaxis of disorders caused by or affected by dysfunction of the 5-HT$_4$ receptor. Such disorders for which the present compounds provide treatment or prophylaxis include pathologies of the central nervous system such as anxiety, pain, depression, schizophrenia, memory disorders, and dementia; pathologies of the gastrointestinal tract such as irritable bowel syndrome, nausea, gastroesophageal reflux disease, dyspepsia, gastrointestinal motility disorders, and constipation; cardiovascular disorders such as atrial fibrillation, arrhythmias and tachycardia; and genitourinary disorders such as urinary retention, urinary incontinence, and pain on urination.

DETAILED DESCRIPTION OF THE INVENTION

In the present document, all expressions of concentration, percent, ratio and the like will be expressed in weight units unless otherwise stated, except for mixtures of solvents which will be expressed in volume units. All temperatures not otherwise stated will be expressed in degrees Celsius.

Compounds

In the general formulas of the present document, the general chemical terms have their usual meanings. For example, the term "C$_1$–C$_3$ alkyl" refers to methyl, ethyl, propyl, and isopropyl. The term "C$_1$–C$_4$ alkyl" includes those encompassed by C$_1$–C$_3$ alkyl in addition to n-butyl, s-butyl, or t-butyl. The term "C$_1$–C$_6$ alkyl" includes those encompassed by C$_1$–C$_4$ alkyl in addition to pentyl, pent-2-yl, pent-3-yl, 2-methylbutyl, 2-methylbut-2-yl, 3-methylbut-2-yl, 3-methylbutyl, 2,2-dimethylpropyl, hexyl, hex-2-yl, hex-3-yl, 2-methylpentyl, 2-methylpent-2-yl, 2-methylpent-3-yl, 4-methylpent-2-yl, 4-methylpentyl, 2,3-dimethylbutyl, 2,3-dimethylbut-2-yl, 2,2-dimethylbutyl, 3,3-dimethylbut-2-yl, and 3,3-dimethylbutyl. The term "C$_3$–C$_6$ cycloalkyl" refers to cyclopropyl, cyclobutyl, cyclopentyl, and cyclohexyl.

The term "C$_1$–C$_4$ alkoxy" refers to methoxy, ethoxy, propoxy, isopropoxy, n-butoxy, s-butoxy, and t-butoxy.

The term "C$_1$–C$_4$ alkylthio" refers to methylthio, ethylthio, propylthio, isopropylthio, n-butylthio, s-butylthio, and t-butylthio.

The terms "substituted C$_3$–C$_6$ cycloalkyl", "substituted phenyl", and "substituted benzoyl" refer respectively to a cycloalkyl, phenyl, and benzoyl group substituted from 1 to 3 times with substituents selected independently from the group consisting of: halo, C$_1$–C$_4$ alkyl, hydroxy, C$_1$–C$_4$ alkoxy, C$_1$–C$_4$ alkylthio, cyano, trifluoromethyl, carboxamido, or mono or di(C$_1$–C$_4$ alkyl)carboxamido.

When R$^4$ and R$^5$ combine with the nitrogen atom to which they are attached to form a heterocyclic group, the heterocyclic group thus formed may be unsubstituted or may be substituted from 1 to 3 times independently with a C$_1$–C$_4$ alkyl group.

The term "halo" and "halide" refers to chloro, fluoro, bromo, and iodo.

The term "carbonyl activating group" refers to a substituent of a carbonyl that promotes nucleophilic addition reactions at that carbonyl. Suitable activating substituents are those which have a net electron withdrawing effect on the carbonyl. Such groups include, but are not limited to, alkoxy, aryloxy, nitrogen containing aromatic heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-tolylsulfonate, and the like; and halides such as chloride, bromide, or iodide.

The term "amino protecting group" as used in this specification refers to substituents of the amino group commonly employed to block or protect the amino functionality while reacting other functional groups on the compound. Examples of such amino-protecting groups include the formyl group, the trityl group, the phtalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivatized amino group is stable to the condition of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by J. S. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1991, Chapter 7, hereafter referred to as "Barton" and "Greene" respectively.

The term "hydroxy activating substituent" refers to a substituent that is singly bonded to an oxygen atom that makes the moiety as a whole, i.e. the group of the formula O-(hydroxy activating substituent), labile to displacement. Typical hydroxy activating substituents include, but are not limited to, p-tolunesulfonyl, phenylsulfonyl, trifluoromethylsulfonyl, isobutoxycarbonyl, acetyl, and the like.

The term "hydroxy activation reagent" refers to organic or inorganic acids, acid halides, and acid anhydrides that are capable of displacing a hydroxy group with a leaving group or converting a hydroxy group into a leaving group labile to base treatment and/or nucleophilic displacement. Typical hydroxy activation agents include, but are not limited to, p-tolunesulfonyl chloride, phenylsulfonyl chloride, trifluoromethylsulfonyl chloride, isobutyl chloroformate, acetyl chloride, thionyl chloride, phosphorus tribromide, and the like. Thionyl chloride or bromide and oxalyl chloride are also hydroxy activating agents.

When $R^2$ and $R^3$ form a bridge of 1 to 4 methylene units, the moiety thus formed, in certain cases, can be locked into an endo or exo isomeric form. Both isomers and mixtures thereof are encompassed within the scope of this invention.

The term "suitable base" refers to any base reactive enough to effect the desired deprotonation without significantly effecting any undesired reactions.

The term "suitable solvent" refers to a solvent which is inert to the ongoing reaction and sufficiently solubilizes the reactants to effect the desired reaction. Examples of suitable solvents include but are not limited to, methylene chloride, chloroform, 1,2-dichloroethane, diethyl ether, acetonitrile, ethyl acetate, 1,3-dimethyl-2-imidazolidinone, tetrahydrofuran, dimethylformamide, toluene, chlorobenzene, dimethylsulfoxide, mixtures thereof, and the like.

The term "pharmaceutically acceptable salt" as used herein, refers to salts of the compounds of formula I which, at the doses administered, are substantially non-toxic to living organisms. Typical pharmaceutically acceptable salts include those salts prepared by reaction of the compounds of the present invention with a mineral or organic acid. Such salts are known as acid addition salts.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, ethanesulfonate, propanesulfonate, naphthalene-1-sulfonate, napthalene-2-sulfonate, mandelate, and the like of a compound of formula I.

While all of the compounds of the present invention are 5-HT$_4$ agents, certain of the compounds are particularly interesting and are preferred. The following listing sets out several groups of preferred compounds. It will be understood that each of the listings may be combined with other listings to create additional groups of preferred compounds.

a) R is hydrogen;
b) R is hydrogen, halo, alkyl, or alkoxy;
c) $R^1$ is hydrogen;
d) $R^1$ is $C_1$–$C_3$ alkyl or $C_3$–$C_6$ cycloalkyl;
e) $R^1$ is hydrogen, methyl, ethyl, propyl, or isopropyl;
f) $R^1$ is hydrogen, isopropyl, s-butyl, pent-2-yl, pent-3-yl, 3-methylbut-2-yl, hex-2-yl, hex-3-yl, 4-methylpent-2-yl, or 4-methylpent-3-yl;
g) $R^2$ and $R^3$ are both hydrogen;
h) $R^2$ and $R^3$ combine to form a bridge of 2 methylene units;
i) $R^2$ and $R^3$ combine to form a bridge of 3 methylene units;
j) X is $OR^4$ and $R^4$ is phenyl substituted from 1 to 3 times with a halogen;
k) X is $NR^4R^5$, $R^5$ is hydrogen, and $R^4$ is benzoyl, benzoyl substituted from 1–3 times independently with halo, hydroxy, $C_1$–$C_4$ alkyl, or $C_1$–$C_4$ alkoxy, or $R^4$ is tricyclo[3.3.1.1$^{3,7}$]decan-1-oyl;
l) $R^4$ S(O)$_2$R$^6$ and $R^6$ is $C_1$–$C_4$ alkyl, phenyl, or phenyl substituted from 1 to 3 times independently with halo, hydroxy, $C_1$–$C_4$ alkyl, or $C_1$–$C_4$ alkoxy;
m) The compound is a pharmaceutically acceptable salt.

The following group is illustrative of compounds contemplated within the scope of this invention:

N-(1-(2-phenoxyethyl)piperidin-4-yl)-1-(2-fluorocyclohexyl)-4-fluoroindazole-3-carboxamide;

N-(8-(N'-(2-methyl-4-hydroxybenzene)sulfonyl)aminomethyl)-8-azabicyclo[3.2.1]octan-3-yl)-2-oxo-3-methyl-5-isopropylbenzimidazole-1-carboxamide;

N-(6-(N'-benzoyl)aminopentyl)-6-azabicyclo[3.1.1]heptan-3-yl)-1-(cyclopentyl)-6-hydroxyindazole-3-carboxamide;

N-(1-(methoxypropyl)piperidin-4-yl)-2-oxo-7-(N-butylcarboxamido)benzimidazole-1-carboxamide;

N-(1-(4-(pyrrolidin-1-yl)butyl)piperidin-4-yl)-1-propyl-6-ethylindazole-3-carboxamide;

N-(1-(hydroxypentyl)piperidin-4-yl)-2-oxo-3-(2,4,6-trimethoxycyclobutyl)-6-ethoxybenzimidazole-1-carboxamide;

N-(9-(O-benzenesulfonyl)hydroxyethyl)-9-azabicyclo[3.3.1]nonan-3-yl)-1-(isopropyl)-4-methylthioindazole-3-carboxamide;

N-(1-(N'-cyclohexyl)aminopropyl)piperidin-4-yl)-2-oxo-3-ethyl-5-cyanobenzimidazole-1-carboxamide;

N-(1-(3-(propylthio)cyclobutoxy)butyl)piperidin-4-yl)-1-cyclopropyl-7-(N,N-dimethylcarboxamido)indazole-3-carboxamide;

N-(10-(N'-3,4-dichlorophenyl)aminopropyl)-10-azabicyclo[4.3.1]decan-3-yl)-2-oxo-3-butyl-6-(N-methyl-N-ethylcarboxamido)benzimidazole-1-carboxamide;

N-(8-(O-methanesulfonyl)hydroxypropyl)-8-azabicyclo[3.2.1]octan-3-yl)-1-(t-butyl)-4-trifluoromethylindazole-3-carboxamide;

N-(1-(N'-cyclohexanesulfonyl)aminopropyl)piperidin-4-yl)-1-carboxamido-2-oxo-3-propyl-6-(carboxamido)benzimidazole;

N-(1-(2-(piperazin-1-yl)ethyl)piperidin-4-yl)1H-indazole-3-carboxamide;

N-(1-(O-tricyclo[3.3.1.1$^{3,7}$]decan-1-oyl)hydroxymethylpiperidin-4-yl)-2-oxo-3-cyclohexyl-5-chlorobenzimidazole-1-carboxamide; and N-(8-(N'-4-cyanocyclopentanesulfonyl)aminoethyl)-8-azabicyclo[3.2.1]octan-3-yl)-1-pentyl-4-methylindazole-3-carboxamide.

Synthesis

The compounds of the present invention are prepared from appropriately substituted 1H-indazole- and 2-oxo-benzamidazoles-3-carboxylic acids or activated acids thereof. Compounds of formula I where X is $OR^4$ may be prepared from compounds of formula II and III as described in Scheme 1 where A—D, n, R, $R^1$, $R^2$, $R^3$, and $R^4$ are as described supra and $R^7$ is a carbonyl activating group.

Scheme 1

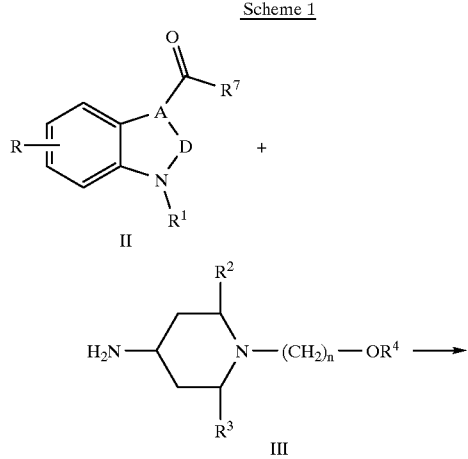

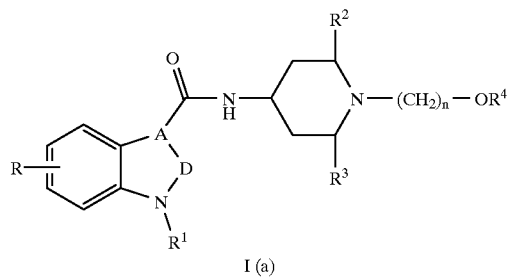

I (a)

The first reaction of Scheme 1 is the formation of a carboxamide by coupling the activated carboxylic acid of formula II and an amine of formula III. Formation of the amide is readily performed by dissolving or suspending the compound of formula III in a suitable solvent and adding a compound of formula II. Tetrahydrofuran, dimethylformamide, or a mixture thereof is usually a convenient and preferred solvent. The compound of formula II is typically employed in a molar excess. For example, a 1.01 to 1.5 molar excess, relative to the compound of formula III is generally employed. A 1.25 to 1.4 molar excess is typically preferred. The preferred carbonyl activating group is halo, specifically chloro or bromo. The reaction is typically carried out at a temperature of from about 0° C. to about 60° C., usually preferably at ambient temperature.

As an alternative, the compound of formula II may be activated and reacted in situ by dissolving or suspending the unactivated compound of formula II (i.e. a compound of formula II where $R^7$ is OH) in a suitable solvent and adding an activating agent. See, e.g., The Peptides, Gross and Meienhofer, Eds., Academic Press (1979), Ch. 2, for such activating agents. Suitable activating agents include reagents such as thionyl bromide, thionyl chloride, oxalyl chloride, and the like, acid halides such as acetic, formic, sulfonic, methanesulfonic, ethanesulfonic, benzenesulfonic, or p-tolylsulfonic acid halides, and the like; and compounds such as dicyclohexylcarbodiimide, carbonyldiimidazole, and the like. Reagents such as benzotriazole, imidazole, N-hydroxysuccinimide, nitrophenol, and pentahalophenols are also included within the definition of activating reagent. The preferred carbonyl activating agent is 1,1'-carbonyldiimidazole, but any carbonyl activating agent may be useful. Once the activation is complete, usually in from 30 minutes to about 3 hours when conducted at a temperature of from about room temperature to about 60° C., the compound of formula III may be added to form the compound of formula I(a). The activating agent and the compound of formula III are typically employed in a equimolar or slight molar excess. For example, an equimolar to a 1.2 molar excess, relative to the compound of formula II is generally employed. An equimolar amount is typically preferred.

Compounds of formula I where X is $NR^4R^5$, $R^4$ is $C_1$–$C_6$ alkyl, $C_3$–$C_6$ cycloalkyl, substituted $C_3$–$C_6$ cycloalkyl, phenyl, or substituted phenyl, and $R^5$ is hydrogen, or $R^4$ and $R^5$ combine with the nitrogen to which they are attached to form a heterocycle, may be prepared from compounds of formula II and IV as described in Scheme 2 where Pg is an amino protecting group, $R^8$ is $C_1$–$C_6$ alkyl, $C_3$–$C_6$ cycloalkyl, substituted $C_3$–$C_6$ cycloalkyl, phenyl, or substituted phenyl, and $R^9$ is hydrogen, or $R^8$ and $R^9$ together with the nitrogen to which they are attached form a 1-pyrrolidinyl, 1-piperazinyl, 1,2,3,4-tetrahydro-2-isoquinolinyl, 2,3-dihydro-1-indolinyl, 4-morpholinyl, 1-piperidinyl, 1-hexamethyleneiminyl, or phthalimidyl ring, and A—D, n, R, $R^1$, $R^2$, $R^3$, and $R^7$ are as described supra.

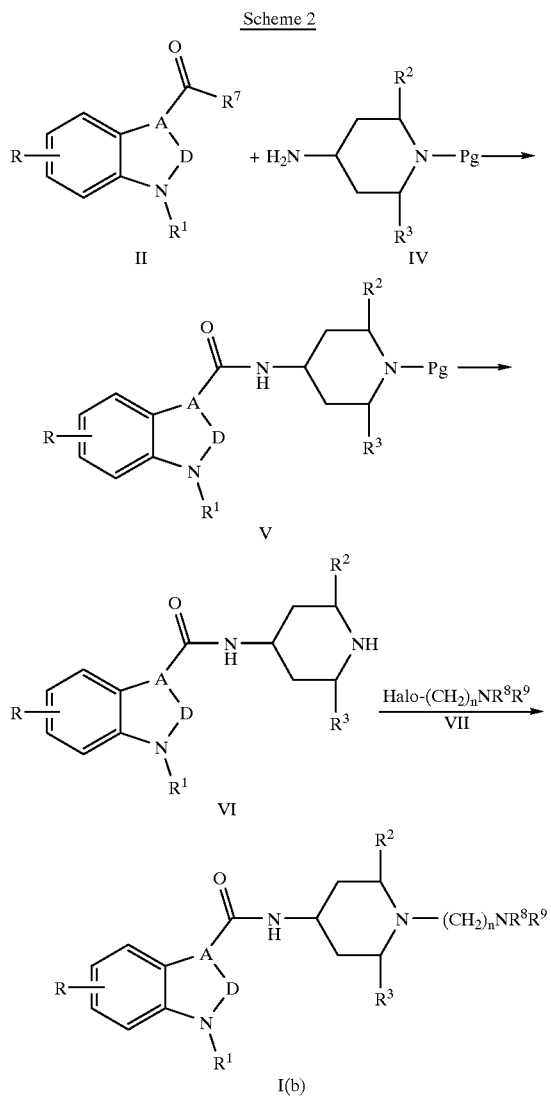

The formation of the carboxamide compound of formula V from the activated carboxylic acid of formula II and an amine of formula IV may be performed as described in Scheme 1 for the formation of compounds of formula I(a).

Compounds of formula VI may then be prepared by removing the amino protecting group (Pg) from compounds of formula V. Choices of protecting groups and methods for their removal may be found in the Barton and Greene references cited above and in the Preparations section which follows.

Compounds of formula I(b) may be prepared by reaction of compounds of formula VI with compounds of formula VII. For example, a compound of formula VI, typically its hydrochloride salt, dissolved or suspended in a suitable solvent in the presence of a suitable base, may be treated with a compound of formula VII. Dimethylformamide is usually a convenient and preferred solvent. Suitable bases include, but are not limited to, carbonates, bicarbonates, and hydroxides (e.g. lithium, sodium, or potassium carbonate, bicarbonate, or hydroxide). Typically, sodium carbonate is the preferred base. The base is generally employed in a substantial molar excess. For example a 3 to 5 molar excess, relative to the compound of formula VI is generally employed. A 4 molar excess is typically preferred. The compound of formula VII is typically and preferably employed in an equimolar amount relative to the compound of formula VI. The reaction is typically carried out at about room temperature when combining the reactants and then at about 100° C. for about 18 hours.

Compounds of formula I where X is $NR^4R^5$ where $R^4$ is hydrogen, $(C_1-C_6$ alkyl)CO, benzoyl, substituted benzoyl, tricyclo[3.3.1.1$^{3,7}$]decan-1-oyl, or $S(O)_2R^6$ and $R^5$ is hydrogen, may be prepared from compounds of formula I(b), where $R^8$ and $R^9$ combine with the nitrogen to which they are attached to form a phthalimidyl ring. This process is shown in Scheme 3 where $R^{10}$ is $C_1-C_6$ alkyl, phenyl, substituted phenyl, adamant-1-yl, or $S(O)_2R^6$ and A—D, n, R, $R^1$, $R^2$, $R^3$, $R^6$ and $R^7$ are as described supra.

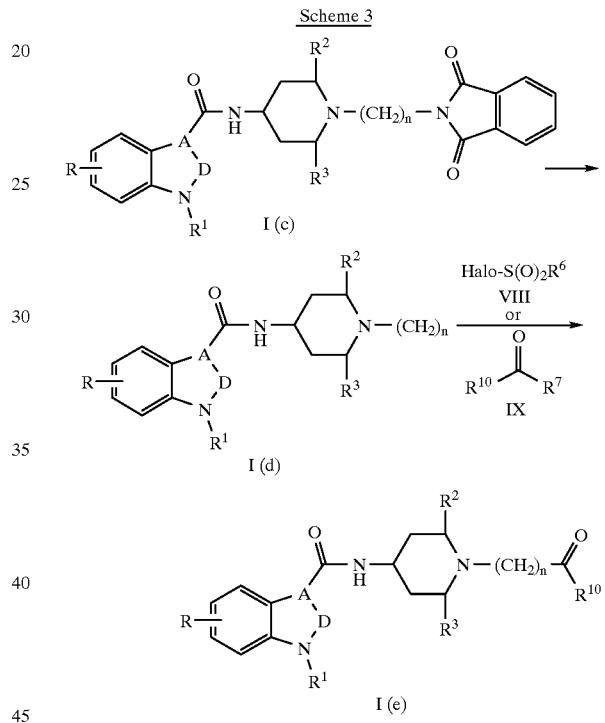

Compounds of formula I(c), prepared as described in Scheme 2, may be converted to other compounds of the invention. For example, compounds of formula I where X is $NR^4R^5$ and $R^4$ and $R^5$ are both hydrogen, may be prepared by removing the phthalimidyl amino protecting group from compounds of formula I(c). Methods for the removal of a phthalimidyl amino protecting group may be found in Greene at 358 or in the Preparations section which follows.

Compounds of formula I(d), prepared as described in the preceding paragraph, may also be converted to other compounds of this invention. For example, a compound of formula I(d), dissolved or suspended in a suitable solvent in the presence of a suitable base, may be treated with a compound of formula VIII to yield the compounds of formula I where X is $NR^4R^5$ where $R^4$ is $S(O)_2R^6$ and $R^5$ is hydrogen. Tetrahydrofuran is usually a convenient and preferred solvent. Suitable bases include, but are not limited to, tri-$(C_1-C_4$ alkyl)amines, carbonates, bicarbonates, and hydroxides (e.g. lithium, sodium, or potassium carbonate, bicarbonate, or hydroxide). Typically, triethylamine is the preferred base. The base is typically employed in a slight molar excess. For example a 1.01 to 1.25 molar excess, relative to the compound of formula I(d) is generally employed. A 1.05 molar excess is typically preferred. The compound of formula VIII is typically and preferably employed in an equimolar amount relative to the compound of formula I(d). The reaction is typically carried out at about room temperature for about 18 hours.

Under the same conditions as the previous paragraph, a compound of formula I(d) may alternatively be treated with a compound of formula IX to afford a compound of formula I where X is $NR^4R^5$, $R^4$ is $(C_1-C_6$ alkyl)CO, benzoyl, substituted benzoyl, or tricyclo[3.3.1.1$^{3,7}$]decan-1-oyl, and $R^5$ is hydrogen.

The $R^1$ substituent (when it is not hydrogen) may be introduced at any convenient point in the reactions of Schemes 1, 2, or 3. For example, a compound of formula I, I(a)–(c), I(e), II, or V where $R^1$ is hydrogen, dissolved or suspended in a suitable solvent in the presence of a suitable base, may be treated with a compound of the formula $R^1$-halo, where halo is preferably bromine or iodine. Dimethylformamide is usually a convenient and preferred solvent. When $R^1$ is being installed onto an unactivated compound of formula II ($R^7$ is hydroxy), a suitable base is lithium, sodium, or potassium hydroxide, preferably potassium hydroxide. When $R^1$ is being installed onto a compound of formula I, I(a)–(c), I(e), II, or V a suitable base is an alkyl metal (e.g. n-butyl lithium, s-butyl lithium, and t-butyl lithium or ethyl magnesium bromide), a metal amide such as lithium diisopropyl amide, a metal alkoxide such as potassium t-butoxide, or metal hydrides (lithium, or potassium hydride) but the preferred base is sodium hydride. The hydroxide base is generally and preferably employed in a molar excess relative to the unactivated compound of formula II, while the hydride base is generally and preferably employed in an equimolar amount relative to the compound of formula I(a)–(c), I(e), II, or V. The reaction is typically carried out at about room temperature for about 90 minutes after adding the base and then for from 2 to 18 hours after adding the compound of the formula $R^1$-halo, typically for about 3 hours.

The pharmaceutically acceptable salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, and the like for acid addition salts. The salts normally precipitate out of solution within about one hour to about ten days and can be isolated by filtration or other conventional methods. For further instruction, see e.g. Berge, S. M, Bighley, L. D., and Monkhouse, D. C., *J. Pharm. Sci.*, 66, 1, 1977.

Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutically acceptable acid addition salts are those formed with mineral acids such as hydrochloric acid, hydrobromic acid, and sulfuric acid, and those formed with organic acids such as maleic acid, tartaric acid, and methanesulfonic acid.

It should be recognized that the particular counterion forming a part of any salt of this invention is not of a critical nature, so long as the salt as a whole is pharmacologically acceptable and as long as the counterion does not contribute undesired qualities to the salt as a whole.

The starting materials for the processes of the present invention may be obtained by a number of routes. For example, compounds of formula III may be prepared according to the route shown in Scheme 4 where $R^{12}$ is chloro, bromo, or a moiety of the formula O-(hydroxy activating substituent) and n, Pg, $R^2$, $R^3$, and $R^4$ are as described supra.

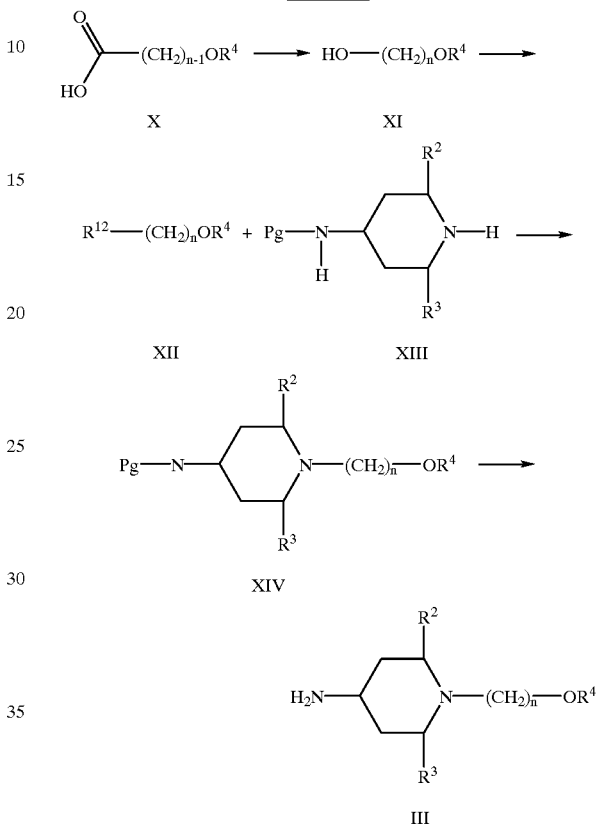

Compounds of formula XI may be prepared from compounds of formula X by methods well known in the art. Methods for reducing carboxylic acids to their corresponding alcohols may be found in Larock, *Comprehensive Organic Transformations*, VCH Publishers, Inc., New York, N.Y., 1989, pgs. 548–552. Specifically, a compound of formula X, dissolved or suspended in a suitable solvent, may be treated with a reducing agent. Tetrahydrofuran is usually a convenient and preferred solvent. Borane is typically a convenient and preferred reducing agent. The reducing agent is typically employed in a molar excess but the magnitude of the excess will vary with the reducing agent employed. For example, when borane is the reducing agent a 1.1 to a 1.6 molar excess, relative to the compound of formula X is generally employed. A 1.35 molar excess is typically preferred. The reaction is typically and preferably performed at about 5° C. when adding the reducing agent then at ambient temperature for about 18 hours.

The alcohol moiety of the resulting product of formula XI may then be converted to a leaving group. For example, a compound of formula XI, dissolved or suspended in a suitable solvent in the presence of a suitable base, may be treated with a hydroxy activating reagent. Suitable bases include, but are not limited to, tri-($C_1-C_4$ alkyl)amines, carbonates, bicarbonates, and hydroxides (e.g. lithium, sodium, or potassium carbonate, bicarbonate, or hydroxide). Pyridine is usually a convenient and preferred solvent and base. A preferred hydroxy activating reagent is p-toluenesulfonyl chloride. The reaction is generally performed at about 5° C. for about 1 to 18 hours.

The leaving group thus installed or formed, i.e. $R^{12}$, in compounds of formula XII, may then be displaced by the amino group of a compound of formula XIII. This may be accomplished by dissolving or suspending a compound of formula XIII in a suitable solvent, in the presence of a suitable base, and adding a compound of formula XII. Dimethylformamide is usually a convenient and preferred solvent. Suitable bases include, but are not limited to, tri-($C_1$–$C_4$ alkyl)amines, carbonates, bicarbonates, and hydroxides (e.g. lithium, sodium, or potassium carbonate, bicarbonate, or hydroxide). Typically, sodium carbonate is the preferred base. The base is typically employed in a molar excess. For example a 2 to 6 molar excess, relative to the compound of formula XIII is generally employed. A 3 molar excess is typically preferred. The compound of formula XII is typically and preferably employed in an equimolar amount relative to the compound of formula XIII. The reaction is typically carried out at about 100° C. for about 18 hours.

Compounds of formula III may then be obtained by removing the amino protecting group (Pg) from compounds of formula XIV. Choices of a protecting group and methods for their removal may be found in the Barton and Greene references cited above and in the Preparations section which follows.

Compounds of formula II where A—D is C=N may be prepared from appropriately substituted 4,5,6,7-tetrahydroindazole-3-carboxylic acid ethyl esters as described in the Preparations section or in Piozzi, F., Umani-Ronchi, A., Merlini, L., *Gazz.Chim.Ital.* 95, 814 (1965), and Burnett, J. P., Ainsworth, C., *J.Org.Chem.* 23, 1382, (1958). These 4,5,6,7-tetrahydroindazole-3-carboxylic acid ethyl esters may be prepared from commercially available starting materials as described in Snyder, H. R.; Brooks, L. A.; Shapiro, S. H. *Organic Synthesis,* Blatt, A. H., Ed., John Wiley & Sons, New York, 1943; Coll. Vol. II, pg. 531 together with Ainsworth, C. *J.Am.Chem.Soc.* 79, 5242, 1957.

Compounds of formula II where A—D is N—C=O may be prepared from appropriately substituted 2-oxobenzimidazoles as described in the Preparations section. These 2-oxobenzimidazoles, when not commercially available, may be prepared from commercially available 1,2-phenylenediamines essentially as described in Yoshida, T., Kambe, N., Murai. S, Sonoda, N., *Tet.Let.,* 3037, (1986) or from commercially available phthalic anhydrides essentially as described in Marburg, S., Grieco, P. A., *Tet.Let.,* 1305, (1966).

Compounds of formula IV, VII–X, and XIII are known in the art, and, to the extent not commercially available are readily synthesized by standard procedures commonly employed in the art.

The optimal time for performing the reactions of Schemes 1–4 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds of formula I(b)–I(d), II, III, V, VI, XI, XII, and XIV are preferably isolated and purified before their use in subsequent reactions. These compounds may crystallize out of the reaction solution during their formation and then be collected by filtration, or the reaction solvent may be removed by extraction, evaporation, or decantation. These intermediate and final products of formula I may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains.

PREPARATIONS

Preparation 1

O-(p-Toluenesulfonyl)-3-(4-Fluorophenoxy) propanol

Step 1: Preparation of 3-(4-Fluorophenoxy)propanol 3-(4-Fluorophenoxy)propanoic acid (16.6 g, 90 mmol) was stirred in 100 mL of tetrahydrofuran under a nitrogen atmosphere. The solution was cooled to 5° C. and borane (120 mL, 120 mmol, 1M in tetrahydrofuran) was added dropwise at a rate to keep the temperature of the reaction near 5° C. Once the addition was complete, the solution was allowed to stir at room temperature overnight. The reaction was then cooled below 10° C. and 18 mL of a tetrahydrofuran/water mixture was added. The tetrahydrofuran was removed by evaporation under reduced pressure and the resulting cloudy mixture was diluted with about 200 mL of water. This mixture was extracted three times with diethyl ether. The combined extracts were washed with water, twice with 10% aqueous sodium bicarbonate, and once with brine. The combined extracts were then dried over sodium sulfate, filtered, and concentrated to give 15.24 g of a product oil. Yield: 99%. MS(FD) M+171.

Step 2: Preparation of O-(p-Toluenesulfonyl)-3-(4-Fluorophenoxy)propanol 3-(4-Fluorophenoxy)propanol (7.55 g, 44 mmol) was stirred in 50 mL of pyridine under a nitrogen atmosphere at 5° C. p-Toluenesulfonyl chloride (9.2 g, 50 mmol) was added in one portion and the resulting solution was allowed to stir at 5° C. for 1 hour and then was placed in a refrigerator set at 5° C. overnight. The reaction was then poured into about 300 mL of ice water. This mixture was extracted three times with diethyl ether. The combined extracts were washed 2 times with cold 1N hydrochloric acid and once with cold water. The extracts were then dried over sodium sulfate/potassium carbonate, filtered, and concentrated to give 13.24 g of a solid product. Yield: 93%.

Preparation 2

1-(3-(4-Fluorophenoxy)propyl)-3-Amino-8-Azabicyclo[3.2.1]octane

Step 1: Preparation of N-(Tropan-4-yl)phthalimide

4-Aminotropane (13.3 g, 95 mmol) was added to sodium bicarbonate (7.98 g, 95 mmol) in 200 mL of water at room temperature. N-Carboethoxyphthalimide (21.9 g, 100 mmol) was then added in one portion and the resulting mixture was allowed to stir at room temperature for about 90 minutes. The precipitate that formed was collected and washed with water. The filter cake was dried in a dessicator and recrystallized from cyclohexane to give 8.74 g of product. Yield: 34%. m.p. 145° C.–147° C. EA calculated for $C_{16}H_{18}N_2O_2$: C, 71.09; H, 6.71; N, 10.36. Found: C, 71.30; H, 6.89; N, 10.50. MS(FD) M+270.

Step 2: Preparation of 3-(Phthalimid-1-yl)-8-Azabicyclo [3.2.1]octane

To N-(tropan-4-yl)phthalimide (8.71 g, 32 mmol) in 170 mL of 1,2 dichloroethane at 5° C. under a nitrogen atmosphere was added 1-chloroethylchloroformate (7.0 mL, 64 mmol) at a rate sufficient to maintain the reaction temperature between 0° C. and 5° C. The resulting solution was allowed to warm to room temperature and then was heated at reflux for 3 hours. The solvent was removed and the residue was taken up in 170 mL of methanol and heated at reflux for 1 hour. The solution was concentrated and the residue was recrystallized from about 200 mL of ethanol to give 6.21 g of product. Yield: 66%. EA calculated for $C_{15}H_{17}N_2O_2Cl$: C, 61.54; H, 5.85; N, 9.57. Found: C, 61.51; H, 5.96; N, 9.68. MS(FD) M+256.

Step 3: Preparation of 3-(Phthalimid-1-yl)-8-(3-(4-Fluorophenoxy)propyl)-8-Azabicyclo[3.2.1]octane Hydrochloride To a solution of 3-(phthalimid-1-yl)-8-azabicyclo[3.2.1] octane (5.00 g, 17 mmol) in 75 mL of dimethylformamide was added sodium carbonate (7.2 g, 68 mmol). O-(p-Toluenesulfonyl)-3-(4-fluorophenoxy)propanol (5.53 g, 17 mmol) in 30 mL of dimethylformamide was then added dropwise and the resulting solution was heated at 100° C. for about 18 hours. The solvent was removed and the residue was diluted with water and extracted 3 times with methylene chloride. The extracts were washed with water and brine, dried over sodium sulfate, filtered, and evaporated under reduced pressure under reduced pressure to give 7.99 g of product. The hydrochloride salt of the product was made by adding one equivalent of hydrochloric acid in ethanol. The precipitate which forms is collected by filtration and recrystallized from about 200 mL of methanol to give 3.39 g of product. Yield: 45%. EA calculated for $C_{24}H_{26}N_2O_3ClF$: C, 64.79; H, 5.89; N, 6.30. Found: C, 64.58; H, 5.86; N, 6.32. MS(FD) M+408.

Step 4: Preparation of 3-Amino-8-(3-(4-Fluorophenoxy) propyl)-8-Azabicyclo[3.2.1]octane 3-(Phthalimid-1-yl)-8-(3-(4-fluorophenoxy)propyl)-8-azabicyclo[3.2.1]octane hydrochloride (3.18 g, 7.8 mmol) was converted to the free base in methylene chloride/water with 1N sodium hydroxide. The layers were separated and the methylene chloride was evaporated under reduced pressure to leave an oil which crystallized. This free base was stirred in 160 mL of ethanol and heated to 60° C. An excess of hydrazine hydrate was then added and the resulting solution was heated at 60° C. for about 4 hours. The reaction was cooled to 0° C. and filtered. The filtrate was evaporated under reduced pressure and the residue was stirred with 100 mL of diethylether and 50 mL of 1N sodium hydroxide. The layers were separated and the ether layer was washed with brine, dried over sodium sulfate, and evaporated under reduced pressure to give 1.97 g of an oil which slowly crystallized. Yield: 91%. MS(FD) M+278.

Preparation 3

1-(3-(4-Fluorophenoxy)propyl)-4-Aminopiperidine

Step 1: Preparation of N-Acetyl-1-Benzyl-4-Aminopiperidine

To a solution of 1-benzyl-4-aminopiperidine (19.0 g, 100 mmol) in 300 mL of tetrahydrofuran under a nitrogen atmosphere at room temperature was added triethylamine (15 mL, 105 mmol) followed by a solution of acetyl chloride (7.1 mL, 100 mmol) in 80 mL of tetrahydrofuran keeping the temperature at about 25° C. with the occasional use of an ice bath. The resulting solution was allowed to stir for about 18 hours. The precipitate which formed was filtered and washed with tetrahydrofuran and the filtrate evaporated under reduced pressure to a solid. The solid was recrystallized from about 200 mL of ethyl acetate to give 17.7 g of product. Yield: 76%. EA calculated for $C_{14}H_{20}N_2O$: C, 72.38; H, 8.68; N, 12.06. Found: C, 72.22; H, 8.64; N, 12.29. MS(FD) M+232.

Step 2: Preparation of N-Acetyl-4-Aminopiperidine

A solution of N-acetyl-1-benzyl-4-aminopiperidine (17.4 g, 75 mmol) and palladium catalyst in ethanol was treated with hydrogen gas. The ethanol was evaporated under reduced pressure to give a solid which was recrystallized from about 120 mL of ethyl acetate to give 6.32 g of product. Yield: 59%. MS(FD) M+142.

Step 3: Preparation of N-Acetyl-1-(3-(4-Fluorophenoxy) propyl)-4-Aminopiperidine N-Acetyl-4-aminopiperidine (5.80 g, 41 mmol) and O-(p-toluenesulfonyl)-3-(4-fluorophenoxy)propanol (13.24 g, 41 mmol) were converted to the title compound by the procedure of Preparation 2, Step 3 to give a crude product which was recrystallized from ethyl acetate to give 7.82 g of the title compound. Yield: 65%. m.p. 134° C.–136° C. EA calculated for $C_{16}H_{23}N_2O_2F$: C, 65.28; H, 7.88; N, 9.52. Found: C, 65.49; H, 7.91; N, 9.54. MS(FD) M+1 295.

Step 4: Preparation of 1-(3-(4-Fluorophenoxy)propyl)-4-Aminopiperidine

N-Acetyl-1-(3-(4-fluorophenoxy)propyl)-4-aminopiperidine (7.7 g, 26 mmol) was mixed with 50 mL of ethanol and 50 mL of 5N sodium hydroxide. The resulting solution was heated at reflux for about 72 hours. The ethanol was removed and the residue was diluted with water and extracted 3 times with methylene chloride. The extracts were washed with water and brine, dried over sodium sulfate, filtered, and evaporated under reduced pressure to give 5.58 g of an oil. Yield: 85%. MS(FD) M+252.

Preparation 4

2-Oxobenzimidazole-1-Carboxylic Acid Chloride

To a 1 L, 3-neck round bottom flask fitted with a thermometer, condenser, and an addition funnel was placed 2-hydroxybenzimidazole (36.9 g, 275 mmol), 275 mg of activated charcoal, and 750 mL of dry tetrahydrofuran. The bis(trichloromethyl)carbonate (36.3 g, 122 mmol), dissolved in 100 mL of tetrahydrofuran, was added dropwise at room temperature. The addition funnel was replaced with a gas outlet tube that was dipped into an aqueous concentrated ammonium hydroxide trap. The mixture was heated at reflux for about 18 hours. The solids which formed were filtered and the filtrate was evaporated under reduced pressure to give 61.64 g of a white solid which was used in subsequent reactions without further purification. Yield: >100%.

Preparation 5

Indazole-3-Carboxylic Acid

A mixture of 4,5,6,7-tetrahydroindazole-3-carboxylic acid ethyl ester (21.0 g, 108 mmol), 5% palladium on carbon (7.0 g solid, 3.29 mmol of Pd), and 210 mL of cymene was heated to reflux for 38 hours. At this point complete conversion to the indazole-3-carboxylic acid ethyl ester was shown by TLC (silica gel, 3:1 ethyl acetate-heptane). The reaction was cooled to 120° C. and the 5% palladium on carbon was removed by filtration. The filtrate was combined with 216 mL of 1N sodium hydroxide and tetrabutylammonium hydroxide (1 mL, 1M in methanol). The reaction temperature was maintained at 95° C. for 90 minutes. After cooling to ambient temperature, the phases were separated. The aqueous phase was washed with 50 mL of heptane, then treated with activated carbon (3.0 g) for 30 minutes and filtered. A precipitate formed upon neutralization to pH 4.0 with 6N hydrochloric acid which was collected by filtration. The filter cake was washed with 50 mL of water, then dried in vacuo (50° C., 10 torr) to 17.5 g of product as a white solid. Yield: 99%. $^1$H NMR (DMSO-d6, 300 MHz) δ 13.8 (br s, 1H), 12.9 (br s, 1H), 8.05 (d, 1H), 7.59 (d, 1H), 7.38 (t, 1H), 7.23 (t, 1H).

Preparation 6

N-(1-Methylpiperidin-4-yl)-2-Oxo-3-Isopropylbenzimidazole-1-Carboxamide

Step 1: Preparation of N-(1-Methylpiperidin-4-yl)-2-Oxobenzamidazole-1-Carboxamide To a solution of 4-amino-1-methylpiperidine (500 mg, 4.4 mmol) under a nitrogen atmosphere in about 12 mL of tetrahydrofuran was added 2-oxobenzimidazole-1-carboxylic acid chloride (1.2 g, 6.1 mmol) in portions. A rise in temperature was observed and a thick yellow oil was formed. The reaction was allowed to stir at room temperature for about 72 hours. The tetrahydrofuran was evaporated under reduced pressure and the residue taken up in 1N hydrochloric acid. This solution was washed twice with ethyl acetate and then made basic (about pH 10) with 2N sodium hydroxide. The basic solution was extracted 4 times with methylene chloride, and the extracts were washed twice with water and once with brine, dried over sodium sulfate, filtered, and evaporated under reduced pressure to 410 mg of a yellow foam. The product was used as is without further purification. Yield: 34%. MS(FD) M+274.

Step 2: Preparation of N-(1-Methylpiperidin-4-yl)-2-Oxo-3-Isopropylbenzimidazole-1-Carboxamide To a solution of N-(1-methylpiperidin-4-yl)-2-oxobenzamidazole-1-carboxamide in about 15 mL of dry dimethylformamide at room temperature under a nitrogen atmosphere was added sodium hydride (60% dispersion in mineral oil, 61 mg, 1.5 mmol). After the hydrogen gas evolution ceased (about 20 minutes), 2-iodopropane (272 mg, 1.6 mmol) was added and the resulting solution was allowed to stir at room temperature for 2 hours. The solvents were removed and the residue was taken up in 1N hydrochloric acid. This solution was washed twice with ethyl acetate. The aqueous layer was made basic (abut pH 10) with saturated aqueous sodium carbonate and extracted twice with methylene chloride. The extracts were washed twice with water and once with brine, dried over sodium sulfate, filtered, and evaporated under reduced pressure. The crude residue was purified via flash chromatography (silica gel, methylene chloride:methanol:ammonium hydroxide, 100:5:1) to give 130 mg of the free base which was converted to the hydrochloride salt. The salt was recrystallized from ethyl acetate/methanol to give 100 mg of an off white solid. Yield: 19%. m.p. 203.5° C.–205° C. EA calculated for $C_{17}H_{25}N_4O_2$: C, 57.87; H, 7.14; N, 15.88. Found: C, 57.57; H, 7.14; N, 15.68. MS(FD) M+316 (free base).

Preparation 7

N-(Piperidin-4-yl)-1-Isopropylindazole-3-Carboxamide Hydrochloride

Step 1: Preparation of 1-Isopropylindazole-3-Carboxylic Acid

To powdered potassium hydroxide pellets (10.5 g, 160 mmol) in 60 mL of dimethylsulfoxide under a nitrogen atmosphere at room temperature was added indazole-3-carboxylic acid (4.86 g, 30 mmol). The resulting mixture was allowed to stir at room temperature for 45 minutes before 2-bromopropane (8.1 mL, 86 mmol) in 20 mL of dimethlsulfoxide was added keeping the temperature of the reaction near 25° C. The resulting solution was allowed to stir at room temperature for 2.5 hours before it was poured into 400 mL of ice cold water. 10.0 mL of glacial acetic acid were added and the resulting precipitate was collected by filtration. The filtrate was extracted three times with ethyl acetate. The combined extracts were dried over sodium sulfate, filtered, and evaporated under reduced pressure to give a crude solid. The crude solid was purified by preparative HPLC using a gradient of methylene chloride, 0 to 15% methanol, 1% acetic acid to give a yellow solid which was recrystallized from ethyl acetate/cyclohexane then from benzene to give 1.04 g of yellow crystals. Yield: 17%. m.p. 160° C.–163° C. EA calculated for $C_{11}H_{12}N_2O_2$: C, 64.69; H, 5.92; N, 13.72. Found: C, 64.79; H, 5.95; N, 13.63. MS(FD) M+204.

Step 2: Preparation of N-(1-Methylpiperidin-4-yl)-1-Isopropylindazole-3-Carboxamide Oxalic Salt To a solution of 1-isopropylindazole-3-carboxylic acid (1.04 g, 5 mmol) in 15 mL of dry tetrahydrofuran under a nitrogen atmosphere was added in one portion 1,1'-carbonyldiimidazole (826 mg, 5 mmol). The resulting solution was allowed to stir at room temperature for 3 hours before a solution of 1-methyl-4-aminopiperidine (582 mg, 5 mmol) in 5 mL of tetrahydrofuran was added. The resulting solution was allowed to stir at room temperature for about 18 hours. The tetrahydrofuran was evaporated under reduced pressure and 50 mL of ethyl acetate was added. This solution was washed with water, cold 1N sodium hydroxide, and brine, dried over sodium sulfate, filtered, and concentrated to an oil. The free base oil was converted to the oxalate salt in warm ethyl acetate and recrystallized from about 30 mL of isopropanol to give 940 mg of colorless crystals. Yield: 48%. EA calculated for $C_{19}H_{26}N_4O_5$: C, 58.45; H, 6.71; N, 14.35. Found: C, 58.20; H, 6.91; N, 14.23. MS(FD) M+300 (free base).

Step 3: Preparation of N-(Piperidin-4-yl)-1-Isopropylindazole-3-Carboxamide Hydrochloride N-(1-Methylpiperidin-4-yl)-1-isopropylindazole-3-carboxamide (2.30 g, 7 mmol) was converted to the title compound by the procedure of Preparation 2, Step 2 to give 800 mg. Yield 33%. MS(FD) M+312.

Preparation 8

Alternate Synthesis of N-(Piperidin-4-yl)-1-Isopropylindazole-3-Carboxamide Hydrochloride Step 1: Preparation of N-(1-Benzylpiperidin-4-yl)-1H-Indazole-3-Carboxamide To a solution of 1H-indazole-3-carboxylic acid (8.11 g, 50 mmol) in 140 mL of dimethylformamide under a nitrogen atmosphere, was added in one portion 1,1'-carbonyldiimidazole. The resulting solution was warmed at 60° C. for 2 hours then cooled to room temperature before adding a solution of 4-amino-1-benzylpiperidine in 20 mL of dimethylformamide in one portion. The resulting solution was heated at 60° C. for 2 hours. The dimethylformamide was evaporated under reduced pressure and the residue dissolved in about 250 mL of methylene chloride. This solution was washed with water, 1N sodium hydroxide, water, and brine, dried over sodium sulfate, filtered, and evaporated under reduced pressure. The residue was recrystallized twice from ethanol to give 10.63 g of light yellow crystals. Yield: 76%. m.p. 198° C.–200° C. EA calculated for $C_{20}H_{22}N_4O$: C, 71.83; H, 6.63; N, 16.75. Found: C, 71.93; H, 6.79; N, 16.70. MS(FD) M+334.

Step 2: Preparation of N-(1-Benzylpiperidin-4-yl)-1-Isopropylindazole-3-Carboxamide Hydrochloride To a solution of N-(1-benzylpiperidin-4-yl)-1H-indazole-3-carboxamide (9.94 g, 29.7 mmol) in 200 mL of dimethylformamide under a nitrogen atmosphere was added sodium hydride (60% dispersion in mineral oil (1.2 g, 30 mmol) and the resulting mixture was allowed to stir at room temperature for 3 hours. The reaction was cooled to about 20° C. and 2-iodopropane (3.3 mL, 33 mmol) was added. The resulting solution was allowed to stir at room temperature for about 18 hours. The dimethylforamide was evaporated under reduced pressure and diluted residue with about 300 mL of ethyl acetate. This solution was washed with 200 mL of 10% aqueous sodium carbonate, water, and brine, dried over sodium sulfate, filtered, and evaporated under reduced pressure to give an oil which crystallized. The crude product was purified via preparative HPLC (silica gel, methylene chloride, 0 to 2% methanol, 0.5% ammonium hydroxide) to give 8.77 g of product. 753 mg (2 mmol) of the free base was stirred in about 30 mL of ethanol and a solution of hydrochloric acid in ethanol was added (2 mM). The mixture was evaporated under reduced pressure and the residue was stirred in about 40 mL of diethyl ether for 2 hours and the resulting precipitate was collected by filtration. The filter cake was recrystallized from ethyl acetate/methanol to give 478 mg of product. Yield: 58%. m.p. 209° C.–212° C. EA calculated for $C_{23}H_{29}N_4ClO$: C, 66.90; H, 7.08; N, 13.57. Found: C, 66.6; H, 7.14; N, 13.46. MS(FD) M+376 (free base).

Step 3: Preparation of N-(Piperidin-4-yl)-1-Isopropylindazole-3-Carboxamide Hydrochloride N-(1-Benzylpiperidin-4-yl)-1-isopropylindazole-3-carboxamide hydrochloride (3.76 g, 10 mmol) was converted to the title compound by the procedure of Preparation 2, Step 2 to give 2.92 g. Yield: 91%. EA calculated for $C_{16}H_{23}N_4ClO$: C, 59.53; H, 7.18; N, 17.35. Found: C, 59.30; H, 7.17; N, 17.25. MS(FD) M+286 (free base).

Preparation 9

N-(8-Azabicyclo[3.2.1]octan-3-yl)-1-Isopropylindazole-3-Carboxamide

Step 1: Preparation of N-(Tropan-4-yl)-1H-Indazole-3-Carboxamide

1H-Indazole-3-carboxylic acid (9.73 g, 60 mmol), 1,1'-carbonyldiimidazole (9.74 g, 60 mmol), and 4-aminotropane (8.42 g, 60 mmol) were converted to the title compound by the procedure of Preparation 7, Step 2 to give 3.02 g. Yield: 18%. m.p. 222° C.–224° C. EA calculated for $C_{16}H_{20}N_4O$: C, 67.58; H, 7.09; N, 19.70. Found: C, 67.65; H, 7.25; N, 19.75. MS(FD) M+284.

Step 2: Preparation of N-(Tropan-4-yl)-1-Isopropylindazole-3-Carboxamide

To a solution of N-(tropan-4-yl)-1H-indazole-3-carboxamide (2.98 g, 10 mmol) in 75 mL of dimethylformamide under a nitrogen atmosphere was added, in portions, sodium hydride (60% dispersion in mineral oil, 420 mg, 10 mmol). The resulting solution was allowed to stir for about 1 hour at room temperature before adding 2-iodopropane (1.2 mL, 12 mmol). This resulting solution was allowed to stir at room temperature for about 18 hours. The dimethylformamide was evaporated under reduced pressure and the residue was dissolved in about 100 mL of 1N hydrochloric acid. The acidic solution was washed with ethyl acetate and then cooled before making it basic with saturated aqueous sodium carbonate. The basic mixture was extracted 3 times with methylene chloride. The extracts were washed with brine, dried over sodium sulfate, filtered, then evaporated under reduced pressure to give a viscous oil. The oil was purified by preparative HPLC (gradient methylene chloride:methanol 0–25%, 1% ammonium hydroxide) to give 2.52 g of an oil. Yield: 77%. MS(FD) M+326.

Step 3: Preparation of N-(8-Azabicyclo[3.2.1]octan-3-yl)-1-Isopropylindazole-3-Carboxamide N-(Tropan-4-yl)-1-isopropylindazole-3-carboxamide (2.30 g, 7 mmol) was converted to the title compound by the procedure of Preparation 2, Step 2 to give 800 mg. Yield: 37%. MS(FD) M+312 (free base).

EXAMPLES

Example 1

N-(8-(3-(4-Fluorophenoxy)propyl)-8-Azabicyclo [3.2.1]octan-8-yl)-2-Oxobenzimidazole-1-Carboxamide Hydrochloride To 1-(3-(4-fluorophenoxy)propyl)-3-amino-8-azabicyclo [3.2.1]octane (557 mg, 2 mmol) dissolved in 10 mL of tetrahydrofuran under a nitrogen atmosphere was added 2-oxobenzimidazole-1-carboxylic acid chloride (492 mg, 2.5 mmol). The resulting mixture was allowed to stir at room temperature for about 18 hours. The tetrahydrofuran was evaporated under reduced pressure and the residue was triturated with about 40 mL of diethyl ether. The crude product was recrystallized from about 25 mL of ethanol to give 560 mg of product. Yield: 57%. EA calculated for $C_{24}H_{28}N_4O_3ClF$: C, 60.69; H, 5.94; N, 11.80. Found: C, 60.41; H, 5.99; N, 11.75. MS(FD) M+439.

Example 2

N-(8-(3-(4-Fluorophenoxy)propyl)-8-Azabicyclo [3.2.1]octan-8-yl)-2-Oxo-3-Isopropylbenzimidazole-1-Carboxamide Hydrochloride N-(8-(3-(4-Fluorophenoxy)propyl)-8-azabicyclo[3.2.1] octan-8-yl)-2-oxobenzimidazole-1-carboxamide hydrochloride (363 mg, 0.83 mmol) was converted to its free base by stirring in methylene chloride/water and adding an excess of 2N sodium hydroxide. An insoluble solid remains after stirring for about 2 hours. The free base was filtered and the filter cake was dissolved in about 3 mL of dimethylformamide under a nitrogen atmosphere. Sodium hydride (33 mg, 0.83 mmol) was added in one portion and the resulting solution was allowed to stir for 90 minutes. 2-Iodopropane (0.1 mL, 1.0 mmol) was added dropwise and the resulting solution was allowed to stir for about 18 hours. The dimethylformamide was evaporated under reduced pressure and the residue was taken up in methylene chloride. This solution was washed with 10% aqueous sodium carbonate, water, and brine, dried over sodium sulfate, filtered, and evaporated under reduced pressure to give 442 mg of an oil which was flash chromatographed (silica gel, 100:2:0.5 methylene chloride:methanol:ammonium hydroxide) to give 290 mg of an oil. The oil was dissolved in diethyl ether and treated with hydrochloric acid/ethanol. The solvents were removed and the residue was recrystallized from ethyl acetate/methanol to give 209 mg. Yield: 49%. m.p. 235° C.–236° C. EA calculated for $C_{27}H_{34}N_4O_3ClF$: C, 62.72; H, 6.63; N, 10.84. Found: C, 62.52; H, 6.64; N, 10.84. MS(FD) M+480 (free base).

Example 3

N-(1-(3-(4-Fluorophenoxy)propyl)piperidin-4-yl)-2-Oxobenzimidazole-1-Carboxamide To a solution of 1-(3-(4-fluorophenoxy)propyl)-4-aminopiperidine (1.84 g, 7 mmol) in 30 mL of tetrahydrofuran under a nitrogen atmosphere at room temperature was added 2-oxobenzimidazole-1-carboxylic acid chloride (1.90 g, 9.7 mmol) in portions. The resulting mixture was allowed to stir for about 18 hours. The tetrahydrofuran was evaporated under reduced pressure and the solid remaining was triturated with diethyl ether. The precipitate was filtered then stirred in a mixture of water and methylene chloride. 2N sodium hydroxide was added to produce the free base and then the layers were separated. The aqueous layer was extracted twice with methylene chloride. The combined organics were washed with brine, dried over sodium sulfate, filtered, and evaporated under reduced pressure to give 2.84 g of solid which was recrystallized from about 40 mL of ethanol to give 1.83 g of product. Yield: 63%. m.p. 169° C.–171° C. EA calculated for: $C_{22}H_{25}N_4O_3$: C, 64.06; H, 6.11; N, 13.58. Found: C, 63.84; H, 6.11; N, 13.69. MS(FD) M+413.

Example 4

N-(1-(3-(4-Fluorophenoxy)propyl)piperidin-4-yl)-2-Oxo-3-Isopropylbenzimidazole-1-Carboxamide Oxalate To a solution of N-(1-(3-(4-fluorophenoxy)propyl) piperidin-4-yl)-2-oxobenzimidazole-1-carboxamide (824 mg, 2.0 mmol) in 15 mL of dimethylformamide under a nitrogen atmosphere was added sodium hydride (60% dispersion in mineral oil, 48 mg, 2.0 mmol). The resulting solution was allowed to stir at room temperature for 1 hour before cooling briefly with an ice bath. 2-Iodopropane (0.24 mL, 2.4 mmol) was then added and the resulting mixture was allowed to stir at room temperature for about 18 hours. The dimethylformamide was evaporated under reduced pressure and the residue was taken up in 10% aqueous sodium carbonate and methylene chloride. The layers were separated and the organics were washed with water and brine, dried over sodium sulfate, filtered, and evaporated under reduced pressure to give 1.01 g of an oil. The crude product was flash chromatographed (silica gel, methylene chloride:methanol 95:5) to give 390 mg of a colorless oil. The oxalate salt was made in warm ethyl acetate and recrystallized from about 20 mL of ethanol to give 342 mg of product. Yield: 31%. EA calculated for $C_{27}H_{33}N_4O_7F$: C, 59.55; H, 6.11; N, 10.29. Found: C, 59.63; H, 6.13; N, 10.25. MS(FD) M+455 (free base).

Example 5

N-(1-(3-(4-Fluorophenoxy)propyl)piperidin-4-yl)-2-Oxo-3-Isopropylbenzimidazole-1-Carboxamide Hydrochloride Salt To a mixture of N-(1-(3-(4-fluorophenoxy)propyl) piperidin-4-yl)-2-oxo-3-isopropylbenzimidazole-1-carboxamide oxalate (180 mg, 0.33 mmol) in methylene chloride/water was added 5N sodium hydroxide. The layers were separated and the organic layer was evaporated under reduced pressure. The residue was taken up in ethyl acetate and an excess of a hydrochloric acid/ethanol solution was added. The solvents were removed and the residue was triturated with ethyl acetate to give 122 mg of product. Yield: 75%. m.p. 210° C.–212° C. EA calculated for $C_{25}H_{32}N_4O_3ClF$: C, 61.15; H, 6.57; N, 11.41. Found: C, 60.89; H, 6.59; N, 11.43. MS(FD) M+454 (free base).

Example 6

N-(1-(3-(4-Fluorophenoxy)propyl)piperidin-4-yl)-3-Carboxamido-1H-Indazole

To a solution of 1H-indazole-3-carboxylic acid (645 mg, 4 mmol) in 10 mL of tetrahydrofuran under a nitrogen atmosphere was added 1,1'-carbonyldiimidazole (645 mg, 4 mmol). The resulting solution was allowed to stir at room temperature for 2 hours before a solution of 1-(3-(4-fluorophenoxy)propyl)-4-aminopiperidine (1.00 g, 4 mmol) in 5 mL of tetrahydrofuran was added. The resulting solution was allowed to stir at room temperature for about 18 hours. The tetrahydrofuran was evaporated under reduced pressure and the residue taken up in about 40 mL of methylene chloride. The solution was washed with water, 10% aqueous ammonium hydroxide, and water, dried over sodium sulfate, filtered, and evaporated under reduced pressure to give a dark red gum. The crude product was purified by flash chromatography (silica gel, methylene chloride:methanol:ammonium hydroxide 100:5:0.5) to give 680 mg of product. Yield: 43%. m.p. 196° C.–198° C. EA calculated for $C_{22}H_{25}N_4O_2F$: C, 66.65; H, 6.36; N, 14.13. Found: C, 66.44; H, 6.45; N, 14.04. MS(FD) M+396.

Example 7

N-(1-(3-(4-Fluorophenoxy)propyl)piperidin-4-yl)-1-Isopropyl-3-Carboxamido-1H-Indazole Hydrochloride To a solution of N-(1-(3-(4-fluorophenoxy)propyl) piperidin-4-yl)-3-carboxamido-1H-indazole (540 mg, 1.36 mmol) in 10 mL of dimethylformamide under a nitrogen atmosphere was added sodium hydride (60% dispersion in mineral oil, 55 mg, 1.36 mmol). The resulting mixture was allowed to stir at room temperature for 1 hour before cooling briefly and adding 2-iodopropane (0.17 mL, 1.63 mmol). The resulting solution was allowed to stir at room temperature for about 18 hours. The dimethylformamide was evaporated under reduced pressure and the residue taken up in methylene chloride. The methylene chloride was washed with 10% aqueous sodium carbonate, water, and brine, dried over sodium sulfate, filtered, and evaporated under reduced pressure to give a red oil. The oil was dissolved in ethanol and one equivalent of concentrated hydrochloric acid was added (0.144 mL). The solution was concentrated to a residue which was stirred in diethyl ether to precipitate the product. The product was collected by filtration then recrystallized from ethyl acetate/methanol to give 406 mg. Yield: 63%. m.p. 174° C.–175° C. EA calculated for $C_{25}H_{32}N_4O_2FCl$: C, 63.21; H, 6.79; N, 11.79. Found: C, 63.50; H, 6.90; N, 11.82. MS(FD) M+438 (free base).

Example 8

N-(8-(3-(4-Fluorophenoxy)propyl)-8-Azabicyclo[3.2.1]octan-8-yl)-1-Isopropylindazole-3-Carboxamide Hydrochloride To a solution of N-(8-azabicyclo[3.2.1]octan-3-yl)-1-isopropylindazole-3-carboxamide (800 mg, 2.6 mmol) in 10 mL of dimethylformamide under a nitrogen atmosphere was added sodium carbonate (672 mg, 6.3 mmol) followed by a solution of O-(p-toluenesulfonyl)-3-(4-fluorophenoxy) propanol (890 mg, 2.7 mmol) in 5 mL of dimethylformamide. The resulting mixture was heated at 100° C. for 18 hours. The dimethylformamide was evaporated under reduced pressure and the residue was taken up in methylene chloride. This solution was washed twice with water and once with brine, dried over sodium sulfate, filtered, and evaporated under reduced pressure to give an oil. The oil was dissolved in ethanol and 1 equivalent (0.22 mL) of concentrated hydrochloric acid was added. The resulting solution was evaporated under reduced pressure to a solid which was stirred in ethyl acetate before filtering. The filter cake was recrystallized from about 20 mL of isopropanol to give 572 mg of product. Yield: 44%. m.p. 245° C.–247° C. EA calculated for $C_{27}H_{34}FN_4O_2Cl$: C, 64.72; H, 6.84; N, 11.18. Found: C, 64.48; H, 6.82; N, 11.08. MS(FD) M+464 (free base).

Example 9

N-(1-(2-(Phthalimid-1-yl)ethyl)piperidin-4-yl)-1-Isopropylindazole-3-Carboxamide Oxalate To a solution of N-(piperidin-4-yl)-1-isopropylindazole-3-carboxamide hydrochloride (2.24 g, 6.9 mmol) in 35 mL of dimethylformamide under a nitrogen atmosphere was added sodium carbonate (2.94 g, 28 mmol). N-(2-bromoethyl)phthalimide (1.76 g, 6.9 mmol) in 10 mL of dimethylformamide was then added and the resulting solution was heated at 100° C. for about 18 hours. The dimethylformamide was evaporated under reduced pressure to a residue which was taken up in about 250 mL of ethyl acetate. The solution was washed with water and brine, dried over sodium sulfate, filtered, and evaporated under reduced pressure to give 3.08 g of the free base product. The free base was purified via flash chromatography (silica gel, ethyl acetate:ethanol 100:5) to give 2.14 g of a viscous oil. 166 mg of the above oil was converted to the oxalate salt in warm ethyl acetate which was collected by filtration and recrystallized from ethyl acetate/methanol to give 130 mg of colorless crystals. Yield: 66%. m.p. 148° C.–150° C. EA calculated for $C_{28}H_{31}N_5O_7$: C, 61.19; H, 5.69; N, 12.74. Found: C, 60.93; H, 5.80; N, 12.59. MS(FD) M+459 (free base).

Example 10

N-(1-(2-Aminoethyl)piperidin-4-yl)-1-Isopropylindazole-3-Carboxamide

To N-(1-(2-(phthalimid-1-yl)ethyl)piperidin-4-yl)-1-isopropylindazole-3-carboxamide (1.86 g, 4.0 mmol) dissolved in 80 mL of ethanol at 60° C. was added an excess of hydrazine hydrate and the resulting solution was stirred at 60° C. for about 4 hours. The reaction was cooled to 0° C. and filtered. The filtrate was evaporated under reduced pressure and to the residue was added 1N sodium hydroxide. This mixture was extracted four times with diethyl ether. The extracts were washed with brine, dried over sodium sulfate, and evaporated under reduced pressure to give 1.21 g of a colorless solid which was used in Examples 12–14 without further purification. Yield: 92%.

Example 11

N-(1-(2-(N'-Methanesulfonyl)aminoethyl)piperidin-4-yl)-1-Isopropylindazole-3-Carboxamide Maleate Salt To N-(1-(2-aminoethyl)piperidin-4-yl)-1-isopropylindazole-3-carboxamide (264 mg, 0.8 mmol) dissolved in 5 mL of tetrahydrofuran under a nitrogen atmosphere at about 15° C. was added triethylamine (0.12 mL, 0.84 mmol) and methanesulfonyl chloride (0.06 mL, 0.8 mmol). The resulting mixture was allowed to stir for about 18 hours at room temperature. The mixture was gravity filtered and the filtrate was evaporated under reduced pressure to give a cloudy oil. The maleate salt was made in warm ethyl acetate and was recrystallized from about 10 mL of ethanol to give 250 mg of colorless crystals. Yield: 60%. EA calculated for $C_{23}H_{33}N_5O_7S$: C, 52.76; H, 6.35; N, 13.38. Found: C, 52.75; H, 6.18; N, 13.17. MS(FD) M+407 (free base).

Example 12

N-(1-(2-(N'-Benzoyl)aminoethyl)piperidin-4-yl)-1-Isopropylindazole-3-Carboxamide Oxalate Salt N-(1-(2-aminoethyl)piperidin-4-yl)-1-isopropylindazole-3-carboxamide (264 mg, 0.8 mmol), triethylamine (0.12 mL, 0.84 mmol), and benzoyl chloride (0.093 mL, 0.8 mmol) were converted to the title compound by the procedure of Example 11, except that the oxalate salt was made instead of the maleate, to give 190 mg. Yield: 45%. EA calculated for $C_{27}H_{33}N_5O_6$: C, 61.94; H, 6.35; N, 13.38. Found: C, 61.89; H, 6.36; N, 13.11. MS(FD) M+433 (free base).

Example 13

N-(1-(2-(N'-tricyclo[$3.3.1.1^{3,7}$]decan-1-oyl)aminoethyl)piperidin-4-yl)-1-Isopropylindazole-3-Carboxamide Oxalate Salt N-(1-(2-aminoethyl)piperidin-4-yl)-1-isopropylindazole-3-carboxamide (264 mg, 0.8 mmol), triethylamine (0.12 mL, 0.84 mmol), and adamantane-1-carboxylic acid chloride (167 mg, 0.8 mmol) were converted to the title compound by the procedure of Example 11 to give 289 mg. Yield: 62%. EA calculated for $C_{31}H_{43}N_5O_6$: C, 64.01; H, 7.45; N, 12.04. Found: C, 64.18; H, 7.61; N, 12.19. MS(FD) M+491 (free base).

Treatment

Representative compounds of the present invention have been biologically tested to demonstrate their interaction with the 5-HT$_4$ receptor. The test was carried out in esophagus smooth muscle, freshly removed from male Wistar rats weighing 250–300 g each. The rats were euthanized by cervical dislocation, and the esophagus was removed and dissected free of connective tissue. The esophagi were used as longitudinal preparations, obtaining two preparations from each animal. The tissues were tied with thread at each end with the lower end being tied to a stationary glass rod and the upper end to a force transducer.

Tissues were mounted in organ baths containing 10 mL of modified Krebs' solution of the following composition (millimolar) NaCl 118.2; KCl 4.6; $CaCl_2 2H_2O$ 1.6; $KH_2PO_4$ 1.2; $MgSO_4$ 1.2; dextrose 10.0; and $NaHCO_3$ 24.8. Tissue bath solutions were maintained at 37° C. and aerated with 95% $O_2$–5% $CO_2$. Tissues were placed under optimum resting force, 1 g, and were allowed to equilibrate for 1 hr before exposure to drugs. Isometric contractions were recorded as changes in grams of force on the Modular Instruments Inc. (Malvern, Pa.) model M4000™ data acquisition system with Sensotec (Columbus, Ohio) model MBL 5514-02™ transducers.

For studies with partial agonists or antagonists, tissues were preincubated with vehicle or antagonist for 45 min. All drugs were prepared daily in deionized water and kept on ice during the course of the experiment. The tissues were contracted by incubation with $10^{-7}$–$10^{-5}$M carbamylcholine, and were relaxed by the addition of serotonin at $10^{-8}$–$10^{-10}$M, which treatment relaxed the tissue and reduced the contraction caused by carbamylcholine. Addition of a representative compound of the present invention antagonized the serotonin response and reduced the observed relaxations of the tissue. Repeated tests of each compound at various concentrations were carried out and the compounds of the invention reduced the observed relaxations at concentrations of 10 μmol or less. This reduction demonstrates that the compounds of the present invention have high affinity for the 5-HT4 receptor.

Furthermore, it is remarkable that compounds of the present invention are markedly more potent in their affinities at the 5-HT$_4$ receptor than in other activities and, for some of the compounds, at other receptors; the selectivity is often shown by concentration differences amounting to two or even more orders of magnitude to achieve the same binding potency.

Accordingly, the methods of the present invention are very potent in affecting the 5-HT$_4$ receptor, and particularly in providing an antagonist effect at that receptor. The methods of the present invention are carried out by administering a compound as described above in an effective dose to a subject in need of such an effect at the 5-HT$_4$ receptor, or in need of treatment or prophylaxis of a dysfunction or disorder of the 5-HT$_4$ receptor. An effective dose, in the contemplation of the present invention, is an amount of compound which is adequate to provide the desired effect, or to provide treatment for the disorder. The compounds are effective, in general, at quite low doses, and are effective over a substantial dosage range. Effective doses will normally fall within the range from about 0.001 to about 30 mg/kg/day of body weight. As usual in pharmaceutical treatments, the daily dose may be administered in a single bolus, or in divided doses, at the judgment of the physician in charge. A more preferred range of doses is from about 0.1 to about 3.0 mg/kg/day. It will be understood by the reader that the dose for a given subject is always to be set by the judgment of the attending physician, and that the dose is subject to modification based on the size of the patient, the lean or fat nature of the subject, the characteristics of the particular compound chosen, the intensity of the subject's symptoms or disease involvement, and perhaps psychological factors which may affect the subject's physiological responses.

The invention is effective in mammals which possess a 5-HT$_4$ receptor; the preferred subject is the human.

As briefly mentioned above, a variety of physiological functions have been shown to be influenced by the 5-HT$_4$ receptor. Accordingly, the methods of the present invention include methods of treatment or prophylaxis of pathologies of the central nervous system such as anxiety, pain, depression, schizophrenia, memory disorders, and dementia; pathologies of the gastrointestinal tract such as irritable bowel syndrome, nausea, gastroesophageal reflux disease, dyspepsia, gastrointestinal motility disorders, and constipation; cardiovascular disorders such as atrial fibrillation, arrhythmias and tachycardia; and genitourinary disorders such as urinary retention, urinary incontinence, and pain on urination. The dosage rates for the treatment of the foregoing disorders are those which have just been mentioned as effective for blocking the 5-HT$_4$ receptor, since treatment or prophylaxis is obtained by activity at that receptor.

Pharmaceutical Compositions

It is customary to formulate pharmaceuticals for administration, to provide control of the dosage and stability of the product in shipment and storage, and the usual methods of formulation are entirely applicable to the compounds of Formula I. Such compositions, comprising at least one pharmaceutically acceptable carrier, are valuable and novel because of the presence of the compounds of Formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired dose and the type of composition to be used. The amount of the compound, however, is best defined as the effective amount, that is, the amount of each compound which provides the desired dose to the patient in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Watermiscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with numerous pores through which the drugs are pumped by osmotic action.

The following typical formulae are provided for the interest and information of the pharmaceutical scientist.

Example 14

Hard gelatin capsules are prepared using the following ingredients:

|  | Quantity (mg/capsule) |
| --- | --- |
| The Compound of Example 2 | 20 mg |
| Starch, dried | 200 mg |
| Magnesium stearate | 10 mg |
| Total | 230 mg |

Example 15

A tablet is prepared using the ingredients below:

|  | Quantity (mg/capsule) |
| --- | --- |
| The Compound of Example 5 | 10 mg |
| Cellulose, microcrystalline | 400 mg |
| Silicon dioxide, fumed | 10 mg |
| Stearic acid | 5 mg |
| Total | 425 mg |

The components are blended and compressed to form tablets each weighing 425 mg.

Example 16

Tablets, each containing 10 mg of active ingredient, are made as follows:

|  | Quantity (mg/capsule) |
| --- | --- |
| The Compound of Example 7 | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The aqueous solution containing polyvinylpyrrolidone is mixed with the resultant with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

Example 17

Capsules, each containing 30 mg of active ingredient, are made as follows:

|  | Quantity (mg/capsule) |
| --- | --- |
| The Compound of Example 8 | 30 mg |
| Starch | 59 mg |
| Microcrystalline cellulose | 59 mg |
| Magnesium stearate | 2 mg |
| Total | 150 mg |

The active ingredient, cellulose, starch, and magnesium stearate are blended, passed through a No. 45 mesh U.S. sieve, and filled into hard gelatin capsules in 150 mg quantities.

Example 18

Suppositories, each containing 5 mg of active ingredient, are made as follows:

|  | Quantity (mg/capsule) |
| --- | --- |
| The Compound of Example 10 | 5 mg |
| Saturated fatty acid glycerides | 2000 mg |
| Total | 2005 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Example 19

Suspensions, each containing 10 mg of active ingredient per 5 mL dose, are made as follows:

|  | Quantity (mg/capsule) |
| --- | --- |
| The Compound of Example 11 | 10 mg |
| Sodium carboxymethylcellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethylcellulose and syrup to form a smooth paste. The benzoic acid solution, flavor and color are diluted with a portion of the water and added, with stirring. Sufficient water is then added to produce the required volume.

Example 20

An intravenous formulation may be prepared as follows:

| | Quantity (mg/capsule) |
|---|---|
| The Compound of Example 12 | 10 mg |
| Isotonic saline | 1000 mL |

We claim:

1. A compound of formula I:

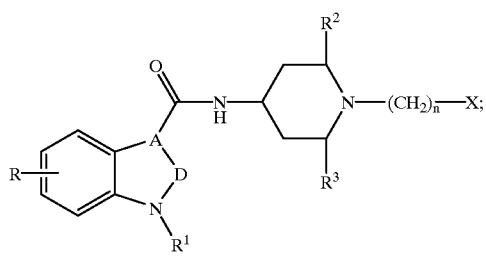

wherein:
A—D is C=N or N—C=O;
n is 1, 2, 3, 4, or 5;
R is hydrogen, halo, $C_1$–$C_4$ alkyl, hydroxy, $C_1$–$C_4$ alkoxy, $C_1$–$C_4$ alkylthio, cyano, trifluoromethyl, carboxamido, mono or di($C_1$–$C_4$ alkyl)carboxamido;
$R^1$ is hydrogen, $C_3$–$C_6$ alkyl, $C_3$–$C_6$ cycloalkyl, or substituted $C_3$–$C_6$ cycloalkyl;
$R^2$ and $R^3$ are each hydrogen;
X is $OR^4$ or $NR^4R^5$;
$R^4$ is hydrogen, $C_1$–$C_6$ alkyl, $C_3$–$C_6$ cycloalkyl, substituted $C_3$–$C_6$ cycloalkyl, phenyl, substituted phenyl, ($C_1$–$C_6$ alkyl)CO, benzoyl, substituted benzoyl, tricyclo[$3.3.1.1^{3,7}$]decan-1-oyl, or $S(O)_2R^6$;
$R^5$ is hydrogen or $R^4$ and $R^5$ together with the nitrogen to which they are attached form a 1-pyrrolidinyl, 1-piperazinyl, 1,2,3,4-tetrahydro-2-isoquinolinyl, 2,3-dihydro-1-indolinyl, 4-morpholinyl, 1-piperidinyl, 1-hexamethyleneiminyl, or phthalimidyl ring;
$R^6$ is $C_1$–$C_6$ alkyl, $C_3$–$C_6$ cycloalkyl, substituted $C_3$–$C_6$ cycloalkyl, phenyl, or substituted phenyl; or a pharmaceutically acceptable salt thereof.

2. A compound of claim 1 wherein n is 2 or 3, R is hydrogen, halo, $C_1$–$C_4$ alkyl, hydroxy, $C_1$–$C_4$ alkoxy, trifluoromethyl, and $R^1$ is $C_1$–$C_4$ alkyl; or a pharmaceutically acceptable salt thereof.

3. A compound of claim 1 wherein X is $NR^4R^5$, $R^4$ is $SO_2R^6$, $R^5$ is hydrogen, and $R^6$ is $C_1$–$C_6$ alkyl, phenyl, or substituted phenyl; or a pharmaceutically acceptable salt thereof.

4. A compound of claim 1 wherein X is $NR^4R^5$, $R^4$ is benzoyl, substituted benzoyl, or tricyclo[$3.3.1.1^{3,7}$]decan-1-oyl, and $R^5$ is hydrogen; or a pharmaceutically acceptable salt thereof.

5. A compound of claim 1 wherein X is $NR^4R^5$ and $R^4$ and $R^5$ together with the nitrogen to which they are attached form a 1-pyrrolidinyl, 1-piperazinyl, 4-morpholinyl, 1-piperidinyl, or phthalimidyl ring; or a pharmaceutically acceptable salt thereof.

6. A compound of claim 1 wherein X is $OR^4$ and $R^4$ is phenyl or substituted phenyl; or a pharmaceutically acceptable salt thereof.

7. The compound of claim 1 which is:
N-(1-(3-(4-Fluorophenoxy)propyl)piperidin-4-yl)-2-Oxo-3-Isopropylbenzimidazole-1-Carboxamide; N-(1-(3-(4-Fluorophenoxy)propyl)piperidin-4-yl)-1-Isopropyl-3-Carboxamido-1H-Indazole; N-(1-(2-(Phthalimid-1-yl)ethyl)piperidin-4-yl)-1-Isopropylbenzimidazole-3-Carboxamide; N-(1-(2-(N'-Methanesulfonyl)aminoethyl)piperidin-4-yl)-1-Isopropylbenzimidazole-3-Carboxamide; N-(1-(2-(N'-Benzoyl)aminoethyl)piperidin-4-yl)-1-Isopropylbenzimidazole-3-Carboxamide; N-(1-(2-(N'-tricyclo[$3.3.1.1^{3,7}$]decan-1-oyl)aminoethyl)piperidin-4-yl)-1-Isopropylbenzimidazole-3-Carboxamide; or a pharmaceutically acceptable salt thereof.

8. A pharmaceutical formulation comprising a pharmaceutically acceptable carrier and a compound of claim 1.

9. A method of providing treatment for anxiety, pain, depression, schizophrenia, memory disorders, dementia, irritable bowel syndrome, nausea, gastroesophageal reflux disease, dyspepsia, gastrointestinal motility disorders, constipation, atrial fibrilation, arrhythmias, tachycardia, urinary retention, urinary incontinence, or pain on urination, comprising administering to a subject in need of such treatment an effective amount of a compound of formula I:

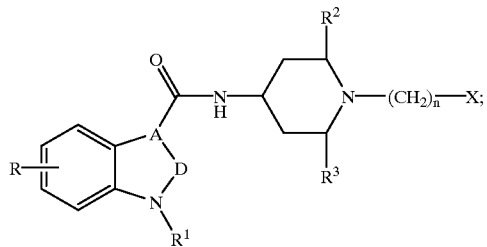

wherein:
A—D is C=N or N—C=O;
n is 1, 2, 3, 4, or 5;
R is hydrogen, halo, $C_1$–$C_4$ alkyl, hydroxy, $C_1$–$C_4$ alkoxy, $C_1$–$C_4$ alkylthio, cyano, trifluoromethyl, carboxamido, mono or di($C_1$–$C_4$ alkyl)carboxamido;
$R^1$ is hydrogen, $C_1$–$C_6$ alkyl, $C_3$–$C_6$ cycloalkyl, or substituted $C_3$–$C_6$ cycloalkyl;
$R^2$ and $R^3$ are each hydrogen;
X is $OR^4$ or $NR^4R^5$;
$R^4$ is hydrogen, $C_1$–$C^6$ alkyl, $C_3$–$C^6$ cycloalkyl, substituted $C_3$–$C_6$ cycloalkyl, phenyl, substituted phenyl, ($C_1$–$C_6$ alkyl)CO, benzoyl, substituted benzoyl, tricyclo[$3.3.1.1^{3,7}$]decan-1-oyl, or $S(O)_2R^6$;
$R^5$ is hydrogen or $R^4$ and $R^5$ together with the nitrogen to which they are attached form a 1-pyrrolidinyl, 1-piperazinyl, 1,2,3,4-tetrahydro-2-isoquinolinyl, 2,3-dihydro-1-indolinyl, 4-morpholinyl, 1-piperidinyl, 1-hexamethyleneiminyl, or phthalimidyl ring;
$R^6$ is $C_1$–$C_6$ alkyl, $C_1$–$C_6$ cycloalkyl, substituted $C_3$–$C_6$ cycloalkyl, phenyl, or substituted phenyl; or a pharmaceutically acceptable salt thereof.

10. A method of claim 9 wherein the compound of formula I is a compound wherein n is 2 or 3, R is hydrogen, halo, $C_1$–$C_4$ alkyl, hydroxy, $C_1$–$C_4$ alkoxy, trifluoromethyl, and $R^1$ is $C_1$–$C_4$ alkyl; or a pharmaceutically acceptable salt thereof.

11. A method of claim 10 wherein the compound of formula I is a compound wherein $R^2$ and $R^3$ are both hydrogen; or a pharmaceutically acceptable salt thereof.

12. A method of claim 11 wherein the compound of formula I is:

N-(1-(3-(4-Fluorophenoxy)propyl)piperidin-4-yl)-2-Oxo-3-Isopropylbenzimidazole-1-Carboxamide; N-(1-(3-(4-Fluorophenoxy)propyl)piperidin-4-yl)-1-Isopropyl-3-Carboxamido-1H-Indazole; N-(1-(2-(Phthalimid-1-yl)ethyl)piperidin-4-yl)-1-Isopropylbenzimidazole-3-Carboxamide; N-(1-(2-(N'-Methanesulfonyl)aminoethyl)piperidin-4-yl)-1-Isopropylbenzimidazole-3-Carboxamide; N-(1-(2-(N'-Benzoyl)aminoethyl)piperidin-4-yl)-1-Isopropylbenzimidazole-3-Carboxamide; N-(1-(2-(N'-tricyclo[3.3.1.1$^{3,7}$]decan-1-oyl)aminoethyl)piperidin-4-yl)-1-Isopropylbenzimidazole-3-Carboxamide; or a pharmaceutically acceptable salt thereof.

\* \* \* \* \*